United States Patent [19]

Malec

[11] 4,278,554
[45] Jul. 14, 1981

[54] ANTIOXIDANT

[75] Inventor: Robert E. Malec, Birmingham, Mich.

[73] Assignee: Ethyl Corporation, Richmond, Va.

[21] Appl. No.: 141,305

[22] Filed: Apr. 18, 1980

Related U.S. Application Data

[62] Division of Ser. No. 966,028, Dec. 4, 1978, Pat. No. 4,222,884.

[51] Int. Cl.$^3$ .................. C10M 1/24; C10M 1/20; C10M 3/18; C10M 3/14
[52] U.S. Cl. .................. 252/52 R; 44/78; 252/404
[58] Field of Search .................. 44/78; 252/52 R, 404

[56] References Cited

U.S. PATENT DOCUMENTS

| | | |
|---|---|---|
| 3,026,264 | 3/1962 | Rocklin et al. .................. 252/52 R |
| 3,211,652 | 10/1965 | Hinkamp .................. 252/49.8 |
| 3,297,575 | 1/1967 | Worrel .................. 252/52 R |
| 4,222,884 | 9/1980 | Malec .................. 252/52 R |

*Primary Examiner*—Delbert E. Gantz
*Assistant Examiner*—Irving Vaughn
*Attorney, Agent, or Firm*—Donald L. Johnson; Joseph D. Odenweller; John F. Hunt

[57] ABSTRACT

Organic material is stabilized against oxidative degradation by the addition of a small amount of an antioxidant compound or mixture of compounds containing a central segment of one to about ten divalent o-hydrocarbyl phenyl groups (e.g. o-tert-butylphenol) bonded to each other through a methylene group and having terminal 3,5-dihydrocarbyl-4-hydroxybenzyl groups at each end. They are made by first condensing o-hydrocarbyl phenol with formaldehyde and then reacting the intermediate with 2,6-dihydrocarbyl phenol and formaldehyde.

13 Claims, No Drawings

ANTIOXIDANT

CROSS REFERENCE TO RELATED APPLICATION

This application is a divisional of application Ser. No. 966,028, filed Dec. 4, 1978 U.S. Pat. No. 4,222,884.

BACKGROUND

Phenolic antioxidants have been used for many years to stabilize organic material against oxidative degradation. For example, 4,4'-methylenebis-(2,6-di-tert-butylphenol) is a commercial antioxidant. Other phenolic antioxidants containing methylene bridges are described in U.S. Pat. No. 3,026,264, U.S. Pat. No. 3,211,652 and U.S. Pat. No. 3,297,575.

SUMMARY

According to the present invention an antioxidant composition is provided which is normally a liquid making it easy to handle and to dissolve in organic substrates. It comprises a central segment of one to about ten methylene bridged o-hydrocarbyl phenol units end-capped with 3,5-dihydrocarbyl-4-hydroxybenzyl groups.

DESCRIPTION OF THE PREFERRED EMBODIMENT

A preferred embodiment of the invention is an antioxidant compound or mixture of compounds having a central segment made up of one to about ten divalent groups having the structure:

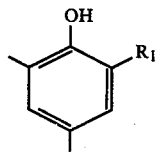

said divalent groups, when there are more than one, being bonded to each other through a —CH$_2$— group, said central segment having a terminal group bonded at each end, said terminal group having the structure:

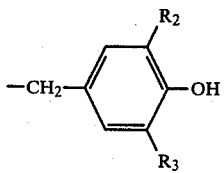

wherein R$_1$ and R$_2$ are selected from the group consisting of α-branched alkyl radicals containing 3 to about 12 carbon atoms, cycloalkyl radicals containing 5 to about 8 carbon atoms and aralkyl radicals containing 8 to about 12 carbon atoms and R$_3$ is selected from the group consisting of alkyl radicals containing 1 to about 12 carbon atoms, cycloalkyl radicals containing 5 to about 8 carbon atoms and aralkyl radicals containing 8 to about 12 carbon atoms.

If the central segment consists of only one o-hydrocarbyl phenol the resultant compound would have the structure:

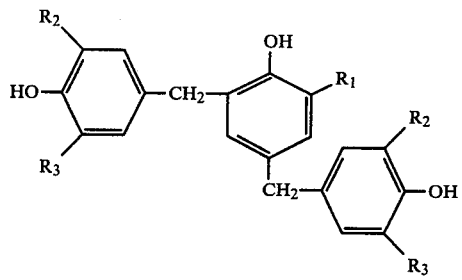

Preferably, the central segment contains two or more o-hydrocarbyl phenol units. Each such unit can be bonded to an adjacent unit through a methylene bridge between two ortho positions, two para positions or ortho-para positions. For example, in the case of a central segment made up of two o-hydrocarbyl phenol units it could have any of the following structures:

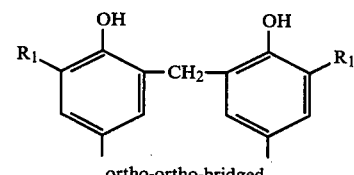
ortho-ortho-bridged

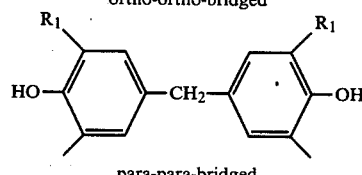
para-para-bridged

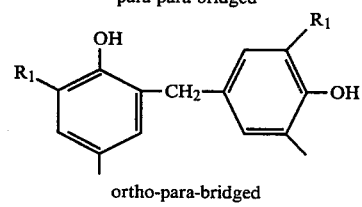
ortho-para-bridged

When the central segment contains three or more o-hydrocarbyl phenol groups, it can contain all ortho-ortho methylene bridges, all para-para methylene bridges, all ortho-para methylene bridges or a mixture of several types. This latter case is represented by the following structure:

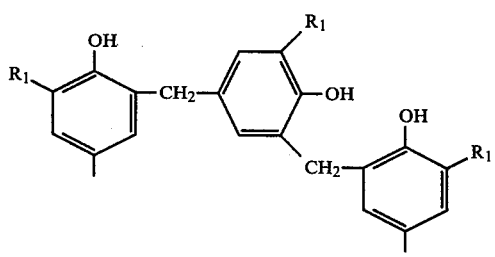

in which the first methylene bridge is ortho-para and the second methylene bridge is ortho-ortho.

It will be apparent from the above that the central segment can grow into a linear chain containing a few or many ortho hydrocarbyl phenol groups bonded through methylene bridges. In practice, the central segment is preferably a mixture of various length chains. Some unreacted o-hydrocarbyl phenol remains, but the preferred components contain from two up to about ten o-hydrocarbyl phenol groups, more preferably, two to about five such groups connected to each other through methylene bridges.

From the above, it can be seen that the end groups of the central segment will have a reactive ortho or para position. These positions are then capped with terminal 3,5-dihydrocarbyl-4-hydroxybenzyl groups. These terminal groups have the structure:

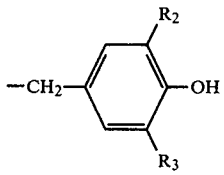

Thus a component containing three o-hydrocarbyl phenol units in the central segment can be represented by the structure:

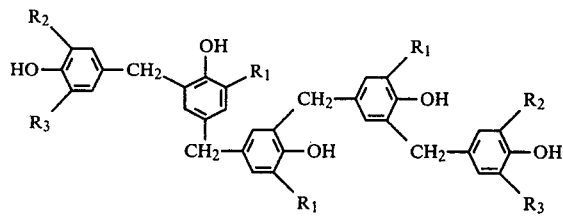

The structure of the principal components of the product can be represented by the following formula:

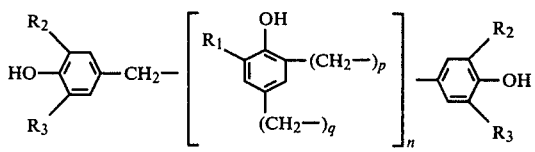

wherein $R_1$, $R_2$ and $R_3$ are as previously defined, n is an interger from 1 to 10 and p and q are 0 or 1 and (p+q) equals 1.

The preferred products are mixtures of structures having different chain lengths and different methylene bridge locations. Because of the many possible structures the products remain liquid and are easily dissolved in most liquid organic substrates such as lubricating oil.

As stated previously, $R_1$ and $R_2$ can be α-branched alkyl groups containing 3 to about 12 carbon atoms. Examples of these are isopropyl, sec-butyl, tert-butyl, tert-octyl, sec-decyl, sec-dodecyl and the like.

Likewise, $R_1$ and $R_2$ can be aralkyl containing 8-12 carbon atoms such as α-methylbenzyl, α,α-dimethylbenzyl, 4-tert-butyl-α-methylbenzyl and the like.

More preferably $R_1$ and $R_2$ are tert-alkyl such as tert-butyl, tert-amyl, tert-octyl and the like.

Most preferably, $R_1$ and $R_2$ are tert-butyl.

$R_3$ can be any alkyl especially those containing from 1 to about 12 carbon atoms such as methyl, ethyl, isopropyl, n-propyl, n-butyl, sec-butyl, tert-butyl, sec-dodecyl and the like.

$R_3$ can also be cycloalkyl or aralkyl as exemplified above.

$R_3$ is preferably a tert-alkyl group containing 4 to about 12 carbon atoms such as tert-butyl, tert-amyl, tert-octyl, tert-dodecyl and the like. More preferably, $R_3$ is a tert-butyl group.

The additives of this invention are made by first condensing an o-hydrocarbyl phenol having the formula

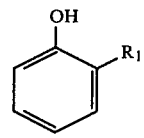

wherein $R_1$ is as previously defined, with formaldehyde using an acidic (e.g. HCl) or basic catalyst. Examples of such o-hydrocarbyl phenols are o-isopropyl phenol, o-sec-butylphenol, o-tert-butylphenol, o-sec-dodecylphenol, o-cyclopentylphenol, o-cyclohexylphenol, o-(α-methylbenzyl)phenol, o-(α,α-dimethylbenzyl)phenol and the like. The more preferred o-hydrocarbyl phenols are o-tert-alkyl phenols. The most preferred is o-tert-butylphenol.

Preferably, the catalyst is an inorganic base. More preferably, it is an alkali metal hydroxide such as sodium hydroxide or potassium hydroxide. The most preferred catalyst is potassium hydroxide.

The amount of catalyst can vary. A useful range is from about 0.05 to about 0.5 mole per mole of o-hydrocarbyl phenol. A preferred range is 0.2–0.3 mole per mole of o-hydrocarbyl phenol.

Formaldehyde can be used as aqueous formaldehyde or in any form that will react as formaldehyde in the reaction system such as para formaldehyde. The amount of formaldehyde can vary from one to about 10 moles per mole of o-hydrocarbyl phenol. A more preferred range is about 1.1–1.5 mole per mole of o-hydrocarbyl phenol.

It is preferred that the reaction be carried out in a solvent. Preferred solvents are alkanols, alkoxyalkanols, and glycol ethers. Examples of these are methanol, ethanol, isopropanol, n-butanol, ethylene glycol, diethylene glycol, triethylene glycol, propylene glycol, ethoxyethanol, diethylene glycol monoethyl ethers and the like. The more preferred solvents are the lower alkanols such as methanol, ethanol, isopropanol, n-propanol, n-butanol and the like. The most preferred solvents are methanol, ethanol and isopropanol.

The amount of solvent can be any amount that provides a solvent effect on the reactant and catalyst. A useful range is about 0.5–10 parts per part of o-hydrocarbyl phenol. A preferred range is about 1–2 parts per part of o-hydrocarbyl phenol.

The reaction is conducted at a temperature high enough to cause the condensation to proceed at a reasonable rate, but not so high as to cause decomposition. A useful range is from about 30° C. up to the boiling point of the reaction mixture. A preferred range is about 40°–90° C.

The reaction should be conducted long enough such that a methylene bridged o-hydrocarbyl phenol chain is formed. This will depend upon the specific reactants, catalysts and temperature and can be determined experimentally with but little effort. A useful range is about 0.5–4 hours. With o-tert-butylphenol using a potassium hydroxide catalyst and a lower alkanol solvent good results are obtained in about 1.5 hours.

After the initial reaction has proceeded to produce the desired central segment, 2,6-dihydrocarbyl phenol is added to end-cap the condensation product. These have the formula:

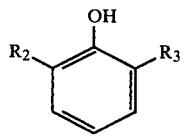

wherein $R_2$ and $R_3$ are as previously defined. Examples of these are 2-isopropyl-6-methylphenol, 2,6-di-sec-butylphenol, 2-methyl-6-tert-butylphenol, 2-methyl-6-tert-octylphenol, 2,6-dicyclopentylphenol, 2,6-di-($\alpha$-methylbenzyl)phenol and the like. The preferred 2,6-dihydrocarbyl phenols are 2,6-di-tert-alkylphenol, most preferably 2,6-di-tert-butylphenol.

The amount of 2,6-dihydrocarbyl phenol added should be an amount sufficient to end-cap the central segments. A useful range is about 0.1–2 moles per mole of o-hydrocarbyl phenol used in the initial reaction. A more preferred range is about 0.3–1.5 moles per mole of initial o-hydrocarbyl phenol.

The end-cap reaction requires the presence of formaldehyde and catalyst. The catalyst added initially will usually suffice. If desired additional catalyst can be added to increase reaction rate.

Residual formaldehyde from the initial reaction can also be used in the end-cap reaction. This is especially useful when a large stoichiometric excess of formaldehyde was used in the initial reaction, say about 3–10 moles per mole of o-hydrocarbyl phenol. Preferably, a small amount of additional formaldehyde is added in the second stage along with the 2,6-dihydrocarbyl phenol. This can be added prior to or during the addition of the 2,6-dihydrocarbyl phenol. The amount added should be an amount which when taken with the residual formaldehyde remaining in the reaction mixture from the first stage will provide sufficient methylene bridges to end-cap the central segments. Good results have been obtained when the total combined moles of formaldehyde used in both stages is about 1.1–2.0 moles per mole of combined phenolic reactants including both o-hydrocarbyl phenol and 2,6-dihydrocarbyl phenol. A preferred range is about 1.1–1.3 moles.

In a highly preferred embodiment about 1.1–1.5 moles of formaldehyde per mole of o-hydrocarbyl phenol are used in the first stage and about 1.1–1.5 moles of formaldehyde per mole of 2,6-dihydrocarbyl phenol are used in the second stage.

It is preferred that the 2,6-dihydrocarbyl phenol be added gradually to the initial reaction mixture while stirring at reaction temperature of about 30° C. up to reflux, more preferably 50°–90° C. This mode minimizes the instantaneous condensation of 2,6-dihydrocarbyl phenol in the reaction mixture and prevents the formation of excessive 4,4'-methylenebis-(2,6-dialkylphenol) which is of much lower solubility and could lead to a precipitate forming in the product. Good results can be obtained when the 2,6-dihydrocarbyl phenol is metered into the reaction over a period of about 15 minutes to 8 hours, more preferably, 0.5–2 hours.

In a highly preferred embodiment the formaldehyde added in the second stage end-capping reaction is also added over an extended period similar to the manner of adding the 2,6-dihydrocarbyl phenol.

Following the end-capping reaction, the product is recovered by standard methods. The recovery can be facilitated by lowering the viscosity of the mixture by adding solvent such as heptane, toluene, dichloromethane and the like. If a base catalyst is used, it is preferred to neutralize this with a weak acid (e.g. acetic acid) to minimize color formation on air exposure. The reaction mixture is then water-washed several times and residual solvents removed by distillation, preferably under vacuum.

Since the product composition is quite complex another preferred embodiment of the invention is a liquid antioxidant composition made by the process comprising (a) in a first step reacting o-tert-alkylphenol with formaldehyde in the presence of an acidic or basic catalyst to form a central segment comprising a chain of o-tert-alkylphenol groups bonded to each other through a —$CH_2$— group and (b) reacting said central segment in the presence of said acidic or basic catalyst with a 2-tert-alkyl-6-alkylphenol and formaldehyde to bond 3-tert-alkyl-4-hydroxy-5-alkylbenzyl terminal groups at each end of said central segment.

In this embodiment the preferred o-hydrocarbyl phenols are o-tert-alkylphenol, most preferably o-tert-butylphenol. The preferred 2,6-dihydrocarbyl phenol is a 2-tert-alkyl-6-alkylphenol such as 2,6-di-tert-butylphenol or 2-methyl-6-tert-butylphenol, especially 2,6-di-tert-butylphenol.

The following example illustrates the manner of making the additives.

EXAMPLE 1

In a reaction vessel was placed 150 gms (1.0 mole) of o-tert-butylphenol, 200 gms methanol, 37.5 gms (1.25 moles) of flaked para formaldehyde and 14 gms (0.25 mole) of potassium hydroxide. The mixture was stirred under nitrogen for 1.5 hours at 55°–60° C. forming the internal segments.

Following this, 227 gms (1.1 moles) of 2,6-di-tert-butylphenol and 120 (1.5 moles) of 38% aqueous formaldehyde solution were separately added over a 2-hour period while the reaction mixture was refluxed (70°–77° C.). The final mixture was heated an additional two hours at reflux. It was then diluted with heptane and acidified with 30 gms of glacial acetic acid. The mixture was water-washed several times and then stripped of volatiles by heating under vacuum. The final product was a viscous yellow liquid weighing 429 gms.

Other additives can be made following the above general procedure, but substituting different o-hydrocarbyl phenols and/or 2,6-dihydrocarbyl phenol according to the previous disclosure.

One particularly preferred mode of operation is to use a crude phenolic mixture containing mainly 2,6-dihydrocarbyl phenol as the source of the end-capping agent. Such mixtures are frequently available in the chemical industry as by-products or residues from other reactions. The following example illustrates such a stream in the second stage.

EXAMPLE 2

In a reaction vessel was placed 300 gms (2 moles) of o-tert-butylphenol, 400 gms of methanol, 75 gms of flaked para formaldehyde and 28 gms of potassium hydroxide. This mixture was stirred under nitrogen for 1.5 hours at 55°–60° C.

Following this, 650 gms of a crude phenolic mixture (appx. 62 weight percent 2,6-di-tert-butylphenol, 8.9 weight percent 2,6-di-tert-butyl-4-hydroxymethyl-phenol, 15.7 weight percent 4,4'-methylenebis-(2,6-ditert-butylphenol), 1.4 weight percent heptane, balance unknown) and 240 gms of 38% aqueous formaldehyde solution were added over a 2-hour period while refluxing the reaction (75°–78° C.). The reaction mixture was then refluxed for another hour and then cooled. It was diluted with heptane and acidified with 60 gms of acetic acid, washed with water several times, dried over anhydrous magnesium sulfate and filtered. The mixture was then stripped of volatiles under vacuum leaving 971 gms of a viscous liquid product. Despite the fact that it contained some 4,4'-methylenebis-(2,6-di-tert-butylphenol) it remained liquid and was soluble in oil in all proportions.

The antioxidants are added to the substrate to be protected in a small but effective amount sufficient to give the required degree of antioxidant protection. This can vary widely within the range of about 0.005–10 weight percent. A preferred range is about 0.05–5 weight percent. Good results are usually achieved using about 0.1–3 weight percent.

The antioxidant can be used in a broad range of organic material normally subject to gradual degradation in the presence of oxygen during use over an extended period. In other words, the organic compositions protected by the present antioxidants are the type in which the art recognizes the need for antioxidant protection and to which an antioxidant of some type is customarily added to obtain an extended service life. The oxidative degradation protected against is the slow gradual deterioration of the organic composition rather than, for example, combustion. In other words, the present additives are not flame retarding additives nor flame suppressing additives and the degradation protected against is not combustion but, rather, the gradual deterioration of the organic composition due to the effects of oxygen over an extended period of time.

Examples of organic materials in which the additives are useful include polymers, both homopolymers and copolymers, of olefinically unsaturated monomers, for example, polyolefins such as polyethylene, polypropylene, polybutadiene, and the like. Also, polyhalohydrocarbons such as polyvinyl chloride, polychloroprene, polyvinylidene chloride, polyfluoro olefins, and the like, are afforded stabilization. The additives provide antioxidant protection in natural and synthetic rubbers such as copolymers of olefinically unsaturated monomers including styrene-butadiene rubber (SBR rubber), ethylene-propylene copolymers, ethylene-propylene-diene terpolymers such as the terpolymer of ethylene, propylene and cyclopentadiene or 1,4-cyclooctadiene. Polybutadiene rubbers such as cis-polybutadiene rubber are protected. Poly-2-chloro-1,3-butadiene (neoprene) and poly-2-methyl-1,3-butadiene (isoprene rubber) are stabilized by the present additives. Likewise, acrylonitrile-butadiene-styrene (ABS) resins are effectively stabilized. Ethylenevinyl acetate copolymers are protected, as are butenemethacrylate copolymers. Nitrogen-containing polymers such as polyurethanes, nitrile rubber, and lauryl acrylate-vinylpyrrolidone copolymers are effectively stabilized. Adhesive compositions such as solutions of polychloroprene (neoprene) in toluene are protected.

Fats and oils of animal and vegetable origin are protected against gradual deterioration. Examples of these are lard, beef tallow, coconut oil, safflower oil, castor oil, babassu oil, cottonseed oil, corn oil, rapeseed oil, tall oil and the like.

Petroleum oils and waxes such as solvent-refined, midcontinent lubricating oil, microcrystalline wax, and Gulf-coast lubricating oils are effectively stabilized.

Animal feeds such as ground corn, cracked wheat, oats, wheat germ, alfalfa, and the like, are protected by mixing a small but effective amount of the present additive with these products. Vitamin extracts, especially the fat-soluble vitamins such as Vitamin A, B, D, E and C, are effectively stabilized against degradation.

The additives are useful in foamed plastics such as expanded polystyrene, polyurethane foams, and the various foamed rubbers, alkyd resins such as short oil terephthalic acid-glycerol-linseed oil resins, and typical long oil resins of trimellitic acid-glycol-tung oil resins including epoxide-modified alkyd resins. Epoxy resins themselves such as isopropylidenebisphenolepichlorohydrin epoxy resins are stabilized against degradation.

Hydrocarbons such as gasoline, kerosene, diesel fuel, fuel oil, furnace oil, and jet fuel are effectively protected. Likewise, synthetic hydrocarbon lubricants, for example α-decene trimer, polybutene lubricants, di- and tri-$C_{12-30}$ alkylated benzene and naphthalene synthetic lubricants are likewise protected.

Organometallics such as tetraethyllead, tetramethyllead, tetravinyllead, ferrocene, methyl ferrocene, cyclopentadienyl manganese tricarbonyl, methyl cyclopentadienyl manganese tricarbonyl, cyclopentadienyl nickel nitrosyl, and the like, are effectively protected against oxidative degradation. Silicone oils and greases are also protected.

Synthetic ester lubricants such as those used in turbines and turbojet engines are given a high degree of stabilization. Typical synthetic ester lubricants include di-2-ethylhexyl sebacate, trimethylolpropane tripelargonate, $C_{5-9}$ aliphatic monocarboxylic esters of pentaerythritol, complex esters formed by condensing under esterifying conditions, mixtures of polyols, polycarboxylic acids, and aliphatic monocarboxylic acids and/or monohydric alkanols. An example of these complex esters is the condensation product formed from adipic acid, ethyleneglycol and a mixture of $C_{5-9}$ aliphatic monocarboxylic acids. Plasticizers such as dioctyl phthalate are effectively protected. Heavy petroleum fractions such as tar and asphalt can also be protected should the need arise.

Polyamides such as adipic acid-1,6-diaminohexane condensates and poly-6-aminohexanoic acid (nylon) are effectively stabilized. Polyalkylene oxides such as copolymers of phenol with ethylene oxide or propylene oxide are stabilized. Polyphenyl ethers such as poly-2,6-dimethylphenyl ether formed by polymerization of 2,6-dimethylphenol using a copper-pyridine catalyst are stabilized. Polycarbonate plastics and other polyformaldehydes are also protected.

Linear polyesters such as phthalic anhydride-glycol condensates are given a high degree of protection. Other polyesters such as trimellitic acid-glycerol condensates are also protected. Polyacrylates such as polymethylacrylate and polymethylmethacrylate are effectively stabilized. Polyacrylonitriles and copolymers of acrylonitriles with other olefinically unsaturated monomers such as methylmethacrylates are also effectively stabilized.

Polyurethanes formed from diisocyanates (e.g. toluene diisocyanate) and polyols and optionally polyamine modifiers are likewise protected against oxidative degradation.

The additives can be used to protect any of the many organic substrates to which an antioxidant is normally added. It can be used where economics permit to protect such substrates as asphalt, paper, fluorocarbons such as teflon, polyvinyl acetate, polyvinylidene chloride, coumarone-indene resins, polyvinyl ethers, polyvinylidene bromide, polyvinyl bromide, acrylonitrile-vinyl bromide copolymer, vinyl butyral resins, silicones such as dimethylsilicone lubricants, phosphate lubricants such as tricresylphosphate, and the like.

The additives are incorporated into the organic substrate in a small but effective amount so as to provide the required antioxidant protection. A useful range is from about 0.005 to about 10 weight percent, and a preferred range is from about 0.05 to 5 weight percent.

Methods of incorporating the additive into the substrate are well known. For example, if the substrate is liquid the additive can be merely mixed into the substrate. Frequently the organic substrate is in solution and the additive is added to the solution and the solvent removed. Solid organic substrates can be merely sprayed with a solution of the additive in a volatile solvent. For example, stabilized grain products result from spraying the grain with a toluene solution of the additive. In the case of rubbery polymers the additive can be added following the polymerization stage by mixing it with the final emulsion or solution polymerization mixture and then coagulating or removing solvent to recover the stabilized polymer. It can also be added at the compounding stage by merely mixing the additive with the rubbery polymer in commercial mixing equipment such as a Banbury blender. In this manner, rubbery polymers such as styrene-butadiene rubber, cis-polybutadiene or isoprene polymers are blended with the antioxidant together with the other ingredients normally added such as carbon black, oil, sulfur, zinc oxide, stearic acid, vulcanization accelerators, and the like. Following mastication, the resultant mixture is fabricated and molded into a finished form and vulcanized. The following will serve to illustrate the manner in which the additives are blended with various organic substrates. The following describes organic compositions containing the additives of the present invention.

EXAMPLE 3

To a synthetic rubber master batch comprising 100 parts of SBR rubber having an average molecular weight of 60,000, 50 parts of mixed zinc propionate stearate, 50 parts carbon black, 5 parts road tar, 2 parts sulfur and 1.5 parts of mercapto benzothiazole is added 1.5 parts of the additive of Example 1. After mastication, the resultant master batch is cured for 60 minutes using 45 psi steam pressure, resulting in a stabilized SBR vulcanizate.

EXAMPLE 4

To 1,000 parts of a solid polypropylene powder is added 5 parts of the additive of Example 2 and 10 parts of dilaurylthiodipropionate. The mixture is heated to its melting point and rapidly stirred and extruded to form a useful polypropylene filament.

EXAMPLE 5

To 100,000 parts of a midcontinent, solvent-refined, mineral oil having a viscosity at 100° F. of 373.8 SUS and at 210° F. of 58.4 SUS is added 500 parts of the additive of Example 1. Following this is added 100 parts of a zinc dialkyldithiophosphate, 50 parts of an over-based calcium alkaryl sulfonate, 1,000 parts of a poly dodecylmethacrylate V.I. improver and 2,000 parts of a 70 percent active oil solution of an alkenyl succinimide of tetraethylenepentamine in which the alkenyl group has a molecular weight of 950. The resultant mixture is blended while warm, following which it is filtered and packaged, giving a stable lubricating oil useful in automotive engines.

From the foregoing, it is apparent how to prepare stable organic compositions using the additives of this invention.

The antioxidants of this invention may be used alone as the sole antioxidant or may be used in combination with other antioxidants or compounds which synergistically affect the effectiveness of the antioxidant. Examples of other antioxidants include 4,4'-methylenebis-(2,6-di-tert-butylphenol), 1,3,5-trimethyl-2,4,6-tri-(3,5-di-tert-butyl-4-hydroxybenzyl)benzene, 2,6-dicyclopentyl-4-methylphenol, 4,4'-thiobis-(6-tert-butyl-m-cresol), 4,4'-butylidenebis-(6-tert-butyl-m-cresol) $\beta$-(3,5-di-tert-butyl-4-hydroxy phenyl) propionic acid pentaerythritol ester and the like.

Particularly preferred synergists are the dialkyl-thio-dipropionates such as dilauryl-thio-dipropionate and distearyl-thio-dipropionate. Such synergists are particularly effective in polyolefin (e.g., polypropylene) compositions and are used in concentrations of about 0.05 to about 0.3 weight percent.

Other synergists are dialkyl phosphites (e.g., dibutylphosphite, trialkylphosphites (e.g., tributylphosphite), dialkyl tin sulfides (e.g., dibutyl tin sulfides) and the like.

Tests have been carried out which show the antioxidant effectiveness of the present additives. In these tests mineral lubricating oil samples were prepared both with and without the additive. The oil was placed in a test cell together with a weighed copper-lead bearing. The cell was heated to 163° C. and air was bubbled through the heated oil for 72 hours at 48 l/hr. The bearing weight loss, acid number and percent viscosity increase was measured. The following results were obtained:

| Additive | Bearing Wt Loss | Acid No. Increase | % Visc. Increase |
|---|---|---|---|
| None | 293.1 mg | 8.9 | 110.5 |
| Ex 1 type | 3.0 mg | 4.3 | 59.1 |

These results demonstrate that the new additives are very effective antioxidants.

I claim:

1. Organic material normally subject to gradual degradation in the presence of oxygen containing an antioxidant amount of a normally liquid antioxidant composition comprising a mixture of compounds having a central segment made up of one to about ten divalent groups having the structure:

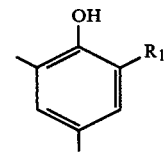

said divalent groups, when there are more than one, being bonded to each other through a —CH$_2$— group, said central segment having a terminal group bonded at each end, said terminal group having the structure:

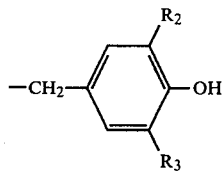

wherein $R_1$ and $R_2$ are selected from the group consisting of α-branched alkyl radicals containing 3 to about 12 carbon atoms, cycloalkyl radicals containing 5 to about 8 carbon atoms and aralkyl radicals containing 8 to about 12 carbon atoms and $R_3$ is selected from the group consisting of alkyl radicals containing 1 to about 12 carbon atoms, cycloalkyl radicals containing 5 to about 8 carbon atoms and aralkyl radicals containing 8 to about 12 carbon atoms.

2. An organic composition of claim 1 wherein $R_1$, $R_2$ and $R_3$ are tert-butyl radicals.

3. An organic composition of claim 1 wherein said organic material is lubricating oil.

4. An organic composition of claim 2 wherein said organic material is lubricating oil.

5. Organic material normally subject to gradual degradation in the presence of oxygen containing an antioxidant amount of a product made by the process comprising
   (A) in a first step reacting o-tert-alkylphenol with formaldehyde in the presence of an acidic or basic catalyst to form a central segment comprising a chain of o-tert-alkylphenol groups bonded to each other through a —$CH_2$— group and
   (B) reacting said central segment in the presence of said acidic or basic catalyst with a 2-tert-alkyl-6-alkylphenol and formaldehyde to bond 3-tert-alkyl-4-hydroxy-5-alkylbenzyl terminal groups at each end of said central segment.

6. A composition of claim 5 wherein said o-tert-alkylphenol is o-tert-butylphenol and said 2-tert-alkyl-6-alkylphenol is 2,6-di-tert-butylphenol.

7. A composition of claim 6 wherein said catalyst is an alkali metal hydroxide.

8. A composition of claim 6 wherein said organic material is lubricating oil.

9. A composition of claim 8 wherein said catalyst is potassium hydroxide.

10. Organic material normally subject to gradual degradation in the presence of oxygen containing an antioxidant amount of a normally liquid antioxidant composition comprising a mixture of methylene-bridged compounds having the structure

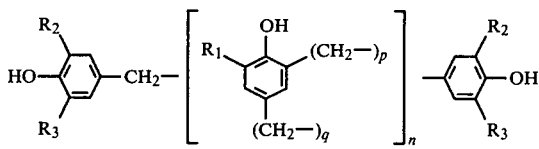

wherein $R_1$ and $R_2$ are selected from the group consisting of α-branched alkyl radicals containing 3 to about 12 carbon atoms, cycloalkyl radicals containing 5 to about 8 carbon atoms and aralkyl radicals containing 8 to about 12 carbon atoms and $R_3$ is selected from the group consisting of alkyl radicals containing 1 to about 12 carbon atoms, cycloalkyl radicals containing 5 to about 8 carbon atoms and aralkyl radicals containing 8 to about 12 carbon atoms, n is an integer from 2 to about 10 and p and q are 0 or 1 and (p+q) equals 1.

11. A composition of claim 10 wherein $R_1$ and $R_2$ are tert-butyl groups.

12. A composition of claim 11 wherein $R_3$ is a tert-butyl group.

13. A composition of claim 12 wherein n is an integer from 2 to about 5.

* * * * *

UNITED STATES PATENT AND TRADEMARK OFFICE
CERTIFICATE OF CORRECTION

PATENT NO. : 4,278,554
DATED : July 14, 1981
INVENTOR(S) : Robert E. Malec

It is certified that error appears in the above—identified patent and that said Letters Patent is hereby corrected as shown below:

The term of this patent subsequent to September 16, 1997, has been disclaimed.

*Signed and Sealed this*

*Twenty-ninth* Day of *December 1981*

[SEAL]

*Attest:*

GERALD J. MOSSINGHOFF

*Attesting Officer*     *Commissioner of Patents and Trademarks*